(12) United States Patent
Matsumoto et al.

(10) Patent No.: US 12,307,721 B2
(45) Date of Patent: May 20, 2025

(54) IMAGING METHOD AND IMAGING APPARATUS

(71) Applicant: Panasonic Intellectual Property Management Co., Ltd., Osaka (JP)

(72) Inventors: Hiroshi Matsumoto, Kanagawa (JP); Hiroki Taoka, Kyoto (JP); Chie Nishi, Kanagawa (JP); Sachiko Takeshita, Tokyo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 422 days.

(21) Appl. No.: 17/664,045

(22) Filed: May 19, 2022

(65) Prior Publication Data
US 2022/0277488 A1    Sep. 1, 2022

Related U.S. Application Data

(63) Continuation of application No. PCT/JP2020/038546, filed on Oct. 12, 2020.

(30) Foreign Application Priority Data

Dec. 6, 2019    (JP) .................................. 2019-221255

(51) Int. Cl.
*G06T 7/90* (2017.01)
*G06T 7/00* (2017.01)
(Continued)

(52) U.S. Cl.
CPC .............. *G06T 7/90* (2017.01); *G06T 7/0002* (2013.01); *G06T 7/50* (2017.01); *G06T 7/64* (2017.01);
(Continued)

(58) Field of Classification Search
CPC .......... G06T 7/90; G06T 7/0002; G06T 7/50; G06T 7/64; G06T 7/70; G06T 11/203;
(Continued)

(56) References Cited

U.S. PATENT DOCUMENTS 7,580,587 B2 *  8/2009  Matsugu .................. H04N 1/62
                                                     382/274
9,787,965 B2 * 10/2017  Tozuka ................. H04N 9/643
(Continued)

FOREIGN PATENT DOCUMENTS

JP    2002-010283    1/2002
JP    2013-137406    7/2013
(Continued)

OTHER PUBLICATIONS

International Search Report of PCT application No. PCT/JP2020/038546 dated Dec. 1, 2020.

*Primary Examiner* — Ali Bayat
(74) *Attorney, Agent, or Firm* — Greenblum and Bernstein, P.L.C.

(57) ABSTRACT

An imaging method is provided which is capable of performing a color measurement easily and appropriately by using a camera. An imaging apparatus captures an image of a face of a user together with a correction device placed close to the face of the user, and identifies a part in the image of the face of the user for which a color measurement is to be performed. The imaging apparatus acquires a colorimetric value of the identified part and corrects the acquired colorimetric value by using the image of the correction device.

17 Claims, 13 Drawing Sheets

(51) Int. Cl.
  *G06T 7/50* (2017.01)
  *G06T 7/64* (2017.01)
  *G06T 7/70* (2017.01)
  *G06T 11/20* (2006.01)
  *G06V 10/56* (2022.01)
  *G06V 40/16* (2022.01)

(52) U.S. Cl.
  CPC .............. *G06T 7/70* (2017.01); *G06T 11/203* (2013.01); *G06V 10/56* (2022.01); *G06V 40/166* (2022.01); *G06T 2207/10024* (2013.01); *G06T 2207/30201* (2013.01); *G06T 2207/30244* (2013.01)

(58) Field of Classification Search
  CPC . G06T 2207/10024; G06T 2207/30201; G06T 2207/30244; G06T 11/00; G06V 10/56; G06V 40/166; G06V 40/162; H04N 23/70; H04N 23/84; H04N 9/45; H04N 23/60; H04N 23/76; A61B 5/00; G01J 3/02; G01J 3/52; G03B 15/00

USPC ........................................................ 382/165
  See application file for complete search history.

(56) References Cited

U.S. PATENT DOCUMENTS

| | | | |
|---|---|---|---|
| 2003/0063300 A1* | 4/2003 | Rubinstenn | H04N 23/61 |
| | | | 358/1.9 |
| 2017/0076444 A1* | 3/2017 | Petit | A61B 5/1032 |
| 2019/0028614 A1* | 1/2019 | De Paepe | G01J 3/522 |
| 2019/0066338 A1* | 2/2019 | Perlman | G06K 19/0614 |
| 2019/0238724 A1* | 8/2019 | Fukase | G01J 3/462 |

FOREIGN PATENT DOCUMENTS

| | | | |
|---|---|---|---|
| JP | 2013137406 A | * 7/2013 | |
| WO | 2005/124302 | 12/2005 | |
| WO | WO-2005124302 A1 | * 12/2005 | ............... G01J 3/50 |

* cited by examiner

IMAGING METHOD AND IMAGING APPARATUS

BACKGROUND

1. Technical Field

The present disclosure relates to an imaging method and an imaging apparatus.

2. Description of the Related Art

To accurately measure the surface color of a human skin or an object, it is common to use a contact-type color measurement instrument that performs spectral analysis, such as a spectrophotometer. However, color measurement instruments are generally expensive and cannot measure a large area at a time because contact points are targets of measurement, and measured values vary depending on the skill of the measurer.

Conventionally, a method has been proposed for displaying a face image such that the image displayed on a display is always corrected so as to have a constant brightness even when conditions such as a brightness vary in an environment in which the image is captured (for example, see Japanese Unexamined Patent Application Publication No. 2002-10283).

SUMMARY

As described above, when the color of a human skin or an object is measured using a color measurement instrument, the measured value varies depending on the skill of the measurer. Therefore, there is a need for a method for measuring a color (a colorimetric value) in a simple and appropriate manner by imaging using a camera.

One non-limiting and exemplary embodiment provides provide an imaging method and an imaging apparatus capable of easily and appropriately performing a color measurement by imaging by a camera.

In one general aspect, the techniques disclosed here feature an imaging method including capturing an image of a face of a person together with a correction device placed close to the face, identifying a part, for which a color measurement is to be performed, in the image of the face, acquiring a colorimetric value of the part, and correcting the colorimetric value using an image of the correction device.

According to one aspect of the present disclosure, it is possible to easily and appropriately perform a color measurement by imaging using a camera.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTIONS

Embodiments of the present disclosure are described in detail referring as necessary to the drawings. However, more detailed explanations than necessary may be omitted. For example, detailed explanations of already well-known matters or duplicate explanations for substantially the same configuration may be omitted. This is to avoid unnecessary redundancy of the following description and to facilitate the understanding of those skilled in the art.

The accompanying drawings and the following description are provided for those skilled in the art to fully understand the present disclosure, and are not intended to limit the subject matter described in the claims.

Figure 1:
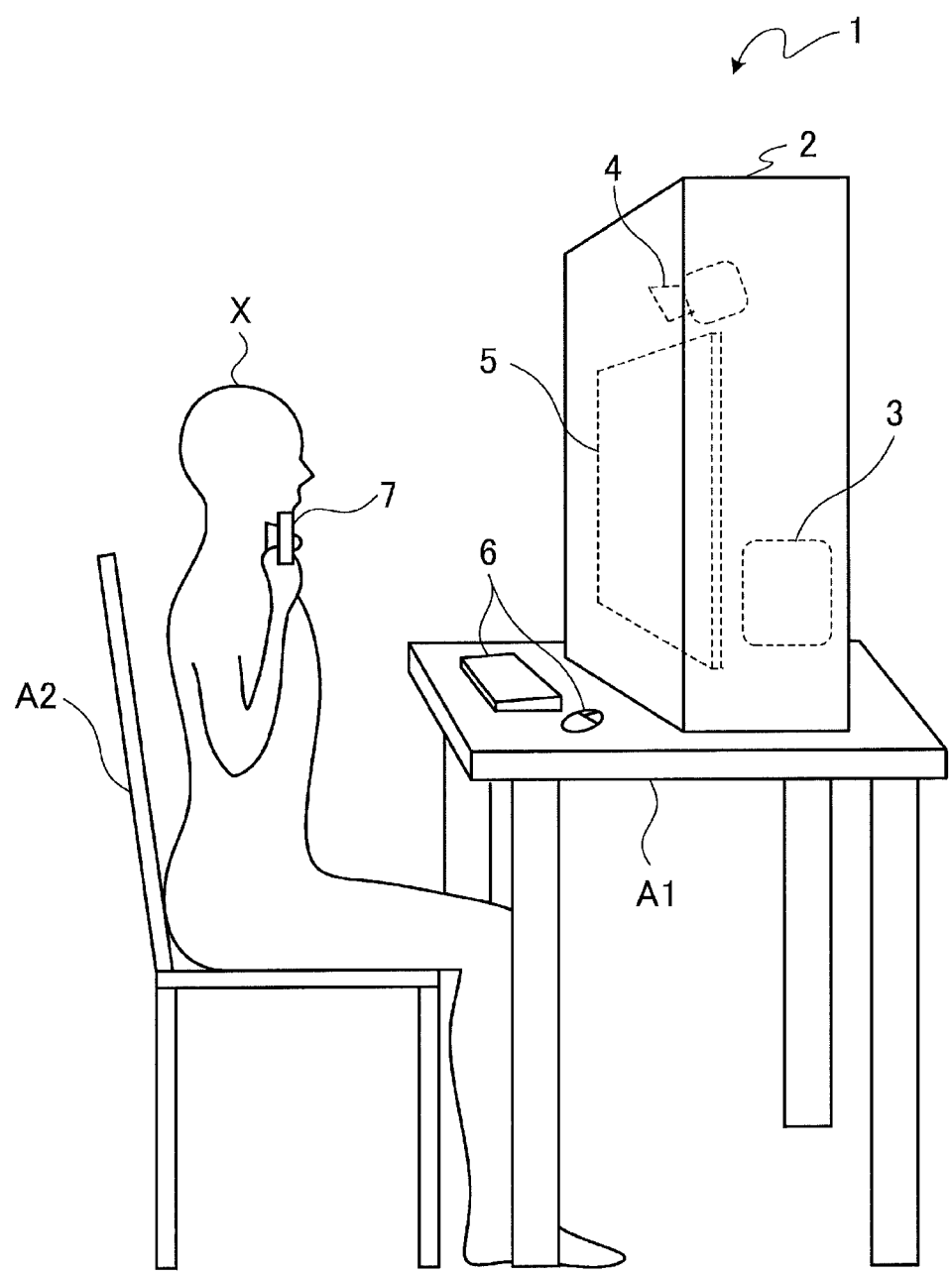
FIG. 1 is a perspective view showing an example of an imaging apparatus according to an embodiment.

FIG. 1 is a perspective view showing an example of an imaging apparatus 1 according to an embodiment. The imaging apparatus 1 is placed on, for example, a desk A1. A chair A2 is disposed in front of the desk A1. A subject X, who to be imaged by the imaging apparatus 1, sits on the chair A2. The subject X is, for example, a person.

The imaging apparatus 1 is installed in, for example, a cosmetic store, a private home, or the like. The imaging apparatus 1 images, for example, a face of the subject X and analyzes blemishes and wrinkles on the face. Based on the result of the analysis, the imaging apparatus 1 proposes, for example, a cosmetic suitable for the subject X.

The imaging apparatus 1 has a main body 2 with a rectangular parallelepiped shape. The main body 2 includes therein a control apparatus 3, a camera 4, and a display 5. The imaging apparatus 1 further includes an input apparatus 6 and a correction device 7.

The camera 4, the display 5, and the input apparatus 6 are connected to the control apparatus 3. The control apparatus 3 images, using the camera 4, the face of the subject X sitting on the chair A2. After the control apparatus 3 images the face of the subject X, the control apparatus 3 detects a cheek of the subject X by using, for example, an image recognition process, and measures a color of the detected cheek.

The camera 4 images the face of the subject X sitting in front of the main body 2 under the control of the control apparatus 3. For example, a half mirror is provided on the front surface of the main body 2 such that the camera 4 is not seen from the front surface of the main body 2.

The face of the subject X imaged by the camera 4 is displayed on the display 5. The display 5 also displays a message guiding a method of operating the imaging apparatus 1, information on cosmetics suitable for the subject X, and the like.

The input apparatus 6 is, for example, a keyboard and a mouse. The input apparatus 6 may be a touch panel provided on the upper surface of the half mirror. The input apparatus 6 accepts, for example, an operation performed by the subject X, and outputs a signal corresponding to the accepted operation to the control apparatus 3.

Figure 3A:
FIG. 3A is a diagram showing an example of a manner of using a correction device as viewed diagonally from the front.
Figure 3B:
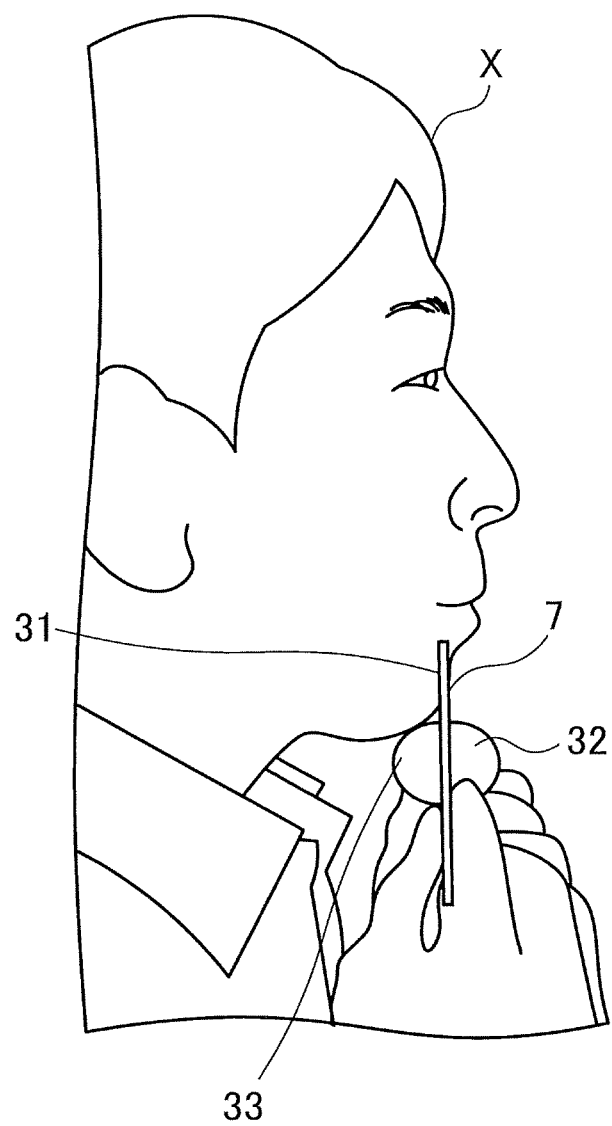
FIG. 3B is a diagram showing an example of a manner of using a correction device as viewed from a side.

The correction device 7 is a device that corrects the colorimetric value of the cheek of the subject X (see, for example, FIGS. 3A and 3B). The correction device 7 is separate from the main body 2. The correction device 7 is imaged together with the face of the subject X. The control apparatus 3 corrects the colorimetric value of the cheek of the subject X by using image data of the correction device 7 imaged together with the face of the subject X.

The outline of the operation of the imaging apparatus 1 shown in FIG. 1 is described below. The operation of the imaging apparatus 1 is divided into, for example, a preparatory operation for storing reference data and a normal operation for imaging the face of the subject X.

First, the preparatory operation is described. In the preparatory operation, the reference data is stored in the imaging apparatus 1. The reference data is stored in the imaging apparatus 1, for example, when the imaging apparatus 1 is installed in a room, when lighting in the room is changed, or when the layout of the room in which the imaging apparatus 1 is installed is changed.

The reference data is used for correcting a colorimetric value acquired in the normal operation of the imaging apparatus 1 described later. The brightness of the subject X caused by the lighting may change, for example, depending on the change in the environment in the room where the imaging apparatus 1 is installed or the distance between the imaging apparatus 1 and the subject X. The change in brightness of the subject X may cause a change in the colorimetric value of the cheek of the subject X. The imaging apparatus 1 corrects the colorimetric value of the cheek of the subject X imaged in the normal operation according to the reference data stored in the preparatory operation.

The reference data is generated from still image data of the correction device 7. For example, the correction device 7 is put in a position similar to a position in which the correction device 7 is put in the normal operation, and the correction device 7 in this position is imaged by the imaging apparatus 1. The control apparatus 3 generates the reference data from the still image data of the imaged correction device 7 and stores the generated reference data in a storage unit. The preparatory operation of the imaging apparatus 1 is performed as described above.

The preparatory operation may be omitted depending on the installation environment. In this case, a fixed value derived by a design or a calculation formula may be applied to the imaging apparatus 1.

Next, the normal operation is described. The subject X sits in front of the imaging apparatus 1. The distance between the face of the subject X and the front surface of the imaging apparatus 1 is, for example, in a range from 50 cm to 55 cm. The subject X performs an operation to image the face of the subject X using the input apparatus 6.

The control apparatus 3 displays a moving image captured by the camera 4 on the display 5 in response to the operation of on the input apparatus 6 to image the face. That is, the control apparatus 3 displays the subject X sitting in front of the imaging apparatus 1 on the display 5 in real time.

The control apparatus 3 displays a message on the display 5 to prompt to place the correction device 7 under the chin of the subject X on the display 5, so as to be superimposed on the moving image captured by the camera 4. Furthermore, the control apparatus 3 displays, for example, an elliptical frame on the display 5 so as to be superimposed on the moving image which is captured by the camera 4 and displayed on the display 5, and the control apparatus 3 displays a message on the display 5 to prompt to put the face in the displayed frame.

When the correction device 7 is appropriately placed under the chin of the subject X such that the face of the subject X fits within the elliptical frame displayed on the display 5, the control apparatus 3 controls the camera 4 to capture a still image of the face of the subject X and the correction device 7. That is, the control apparatus 3 captures the image of the face of the subject X and the correction device 7 together (at the same time). The control apparatus 3 displays the captured still image on the display 5.

The control apparatus 3 performs an image recognition process, separately from the display process of the still image, to detect the cheek of the subject X included in the still image captured by the camera 4, and acquires the colorimetric value of the detected cheek. Furthermore, the control apparatus 3 acquires the image data of the correction device 7 included in the still image captured by the camera 4, by using an image recognition process.

The control apparatus 3 compares the reference data stored in the preparatory operation with the acquired image data of the correction device 7 and calculates a correction value for correcting the colorimetric value of the cheek of the subject X. The control apparatus 3 corrects, by using the calculated correction value, the colorimetric value of the cheek of the subject X acquired from the image data of the still image.

The control apparatus 3 proposes, for example, a cosmetic product suitable for the subject X based on the corrected colorimetric value. For example, the control apparatus 3 proposes a foundation suitable for the cheek color of the subject X. The control apparatus 3 may apply virtual makeup to the face of the subject X displayed in the captured still image. The normal operation of the imaging apparatus 1 is performed as described above.

In the above description, the subject X sits on the chair A2, but this is merely an example. The imaging apparatus 1 may image the subject X in a standing state.

Furthermore, in the above description, the subject X operates the input apparatus 6 to image the subject X, but this is merely an example. For example, in a case where the imaging apparatus 1 is installed in a cosmetics store, a clerk at the cosmetics store may operate the input apparatus 6 to image the subject X.

Furthermore, in the above-description, the imaging apparatus 1 measures the color of the cheek of the subject X, but this is only by way of example. The imaging apparatus 1 may measure the color of a part of the subject X other than the cheek, such as, a forehead, a nose, a chin, or the like. The imaging apparatus 1 may measure colors of two or more parts. The imaging apparatus 1 may measure the color for entire face of the subject X.

The imaging apparatus 1 may be installed in a hospital such as a dermatology hospital. The imaging apparatus 1 may diagnose the skin condition of the face of the subject X from the colorimetric value of the face of the subject X.

Figure 2:
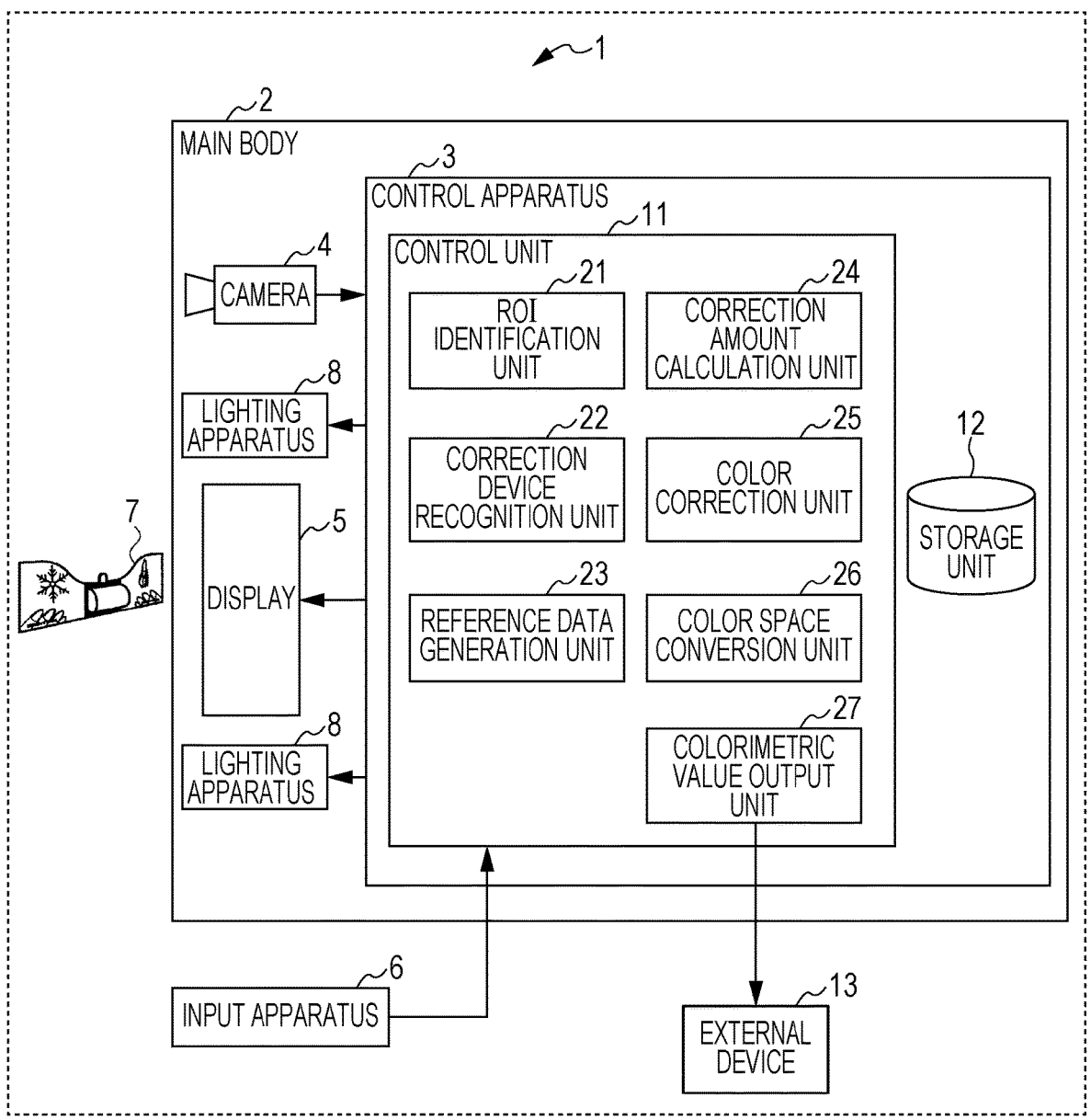
FIG. 2 is a diagram showing an example of a block configuration of an imaging apparatus.

FIG. 2 is a diagram showing an example of a block configuration of the imaging apparatus 1. In FIG. 2, the same constituent elements as those in FIG. 1 are denoted by the same reference numerals. FIG. 2 also shows an external device 13 in addition to the imaging apparatus 1 shown in FIG. 1.

As shown in FIG. 2, the main body 2 includes the control apparatus 3, the camera 4, the display 5, the input apparatus 6, and a lighting apparatus 8.

The lighting apparatus 8 emits light under the control of the control unit 11. For example, the lighting apparatus 8 emits light when the camera 4 captures a still image. The lighting apparatus 8 may be realized using, for example, an LED (Light Emitting Diode).

The control apparatus 3 includes the control unit 11 and a storage unit 12. When a still image is captured using the camera 4, the control unit 11 may turn off the display 5. Alternatively, when a still image is captured using the camera 4, the control unit 11 may display a specific screen on the display 5. This is to prevent the brightness of the face of the subject X from changing due to light emitted by the display 5.

The control unit 11 controls the entire imaging apparatus 1. The control unit 11 may be realized using, for example, a processor such as a CPU (Central Processing Unit).

To realize a particular function, the control unit 11 executes a program stored in, for example, the storage unit 12. The control unit 11 includes, for example, a ROI (Region Of Interest) identification unit 21, a correction device recognition unit 22, a reference data generation unit 23, a correction amount calculation unit 24, a color correction unit 25, a color space conversion unit 26, and a colorimetric value output unit 27.

The ROI identification unit 21 identifies a part, for which the color measurement is to be performed, of the face of the subject X from a still image captured by the camera 4 in a normal operation. For example, the ROI identification unit 21 identifies a cheek of the subject X. Note that the part whose color is measured is not limited to the cheek. The ROI identification unit 21 may change the part whose color is measured according to a signal output from the input apparatus 6.

The correction device recognition unit 22 recognizes (identifies) the correction device 7 in the still image captured by the camera 4.

The reference data generation unit 23 generates reference data from the still image data of the correction device 7 recognized in the preparatory operation by the correction device recognition unit 22. The reference data generation unit 23 stores the generated reference data in the storage unit 12. As will be described later, there are two types of reference data.

The correction amount calculation unit 24 calculates a correction value by which the colorimetric value of the cheek of the subject X is to be corrected, from the reference data stored in the storage unit 12 and the still image data of the correction device 7 recognized in the normal operation by the correction device recognition unit 22.

The color correction unit 25 measures (acquires) the colorimetric value of the cheek of the subject X from the still image data of the cheek of the subject X identified by the ROI identification unit 21. The color correction unit 25 corrects the acquired colorimetric value according to the correction value calculated by the correction amount calculation unit 24.

The color space conversion unit 26 converts the format of the colorimetric value of the cheek of the subject X corrected by the color correction unit 25. For example, the color space conversion unit 26 converts the RGB colorimetric value into an XYZ format or an L*a*b* format.

The colorimetric value output unit 27 outputs the colorimetric value in the format converted by the color space conversion unit 26 to the external device 13. The external device 13 is, for example, a router connected to a USB memory or a network such as the Internet.

The storage unit 12 stores a program for the operation of the control unit 11. The storage unit 12 also stores data used by the control unit 11 in calculation processing, data used by the control unit 11 in controlling various units, and the like. The storage unit 12 may be realized using a storage apparatus such as a RAM (Random Access Memory), a ROM (Read Only Memory), a flash memory, an HDD (Hard Disk Drive), or the like.

FIG. 3A is a diagram showing an example of a manner of using the correction device 7 as viewed diagonally from the front. FIG. 3B is a diagram showing an example of a manner of using the correction device 7 as viewed from a side.

As shown in FIGS. 3A and 3B, the correction device 7 includes a plate part 31 and a color sample part 32. As shown in FIG. 3A, the plate part 31 has a protrusion 41. Furthermore, as shown in FIG. 3B, the correction device 7 also has a support part 33. The plate part 31, the color sample part 32, the support part 33, and the protrusion 41 will be described in detail later with reference to FIGS. 4A to 4C.

As shown in FIGS. 3A and 3B, the correction device 7 is gripped by the subject X. The correction device 7 is placed under the chin of the subject X such that the correction device 7 is in contact with the chin. As shown in FIG. 3B, the correction device 7 is placed such that the front surface of the chin and the plane of the correction device 7 are flush with each other.

That is, the correction device 7 is placed such that the plane of the correction device 7 is flush with the surface of the cheek to be subjected to the color measurement. That is, the correction device 7 is placed close to the face of the subject X such that the distance between the part of the face of the subject X for which the color measurement is to be performed and the main body 2 is substantially equal to the distance between the correction device 7 and the main body 2.

The correction device 7 is imaged by the imaging apparatus 1 together with the subject X in the state shown in FIGS. 3A and 3B.

Figure 4A:
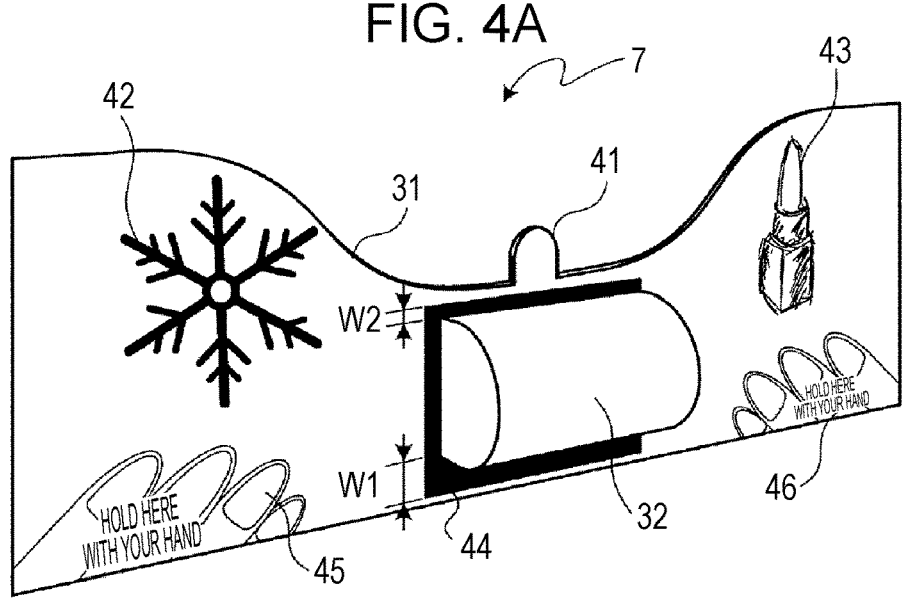
FIG. 4A is a perspective view of a correction device as viewed from a front side.
Figure 4B:
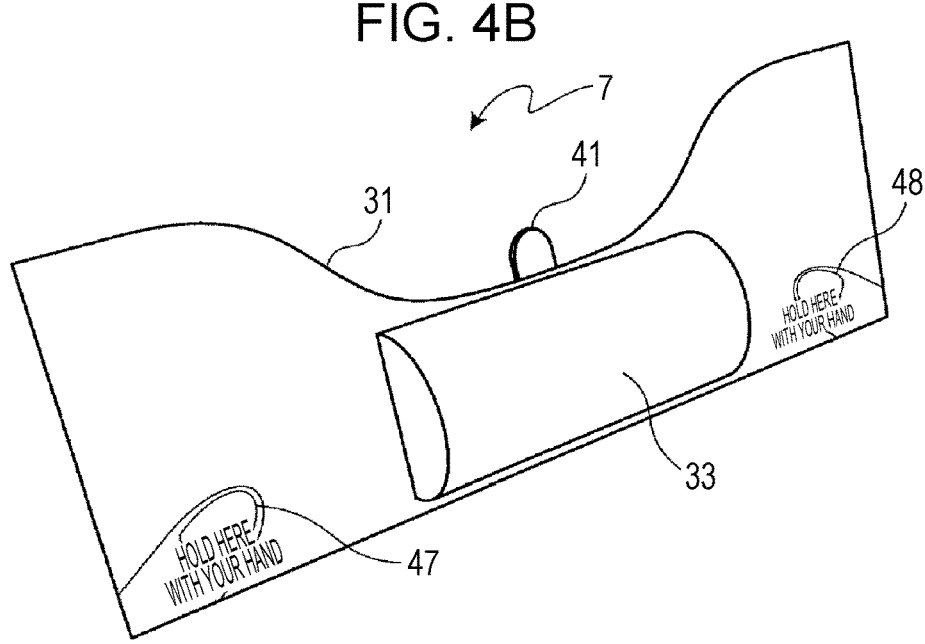
FIG. 4B is a perspective view of a correction device as viewed from a back side.
Figure 4C:
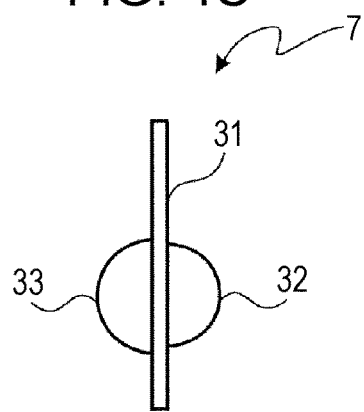
FIG. 4C is a side view of a correction device.

FIG. 4A is a perspective view of the correction device 7 as viewed from the front side. FIG. 4B is a perspective view of the correction device 7 as viewed from the rear side. FIG. 4C is a side view of the correction device 7. Note that the side of the correction device 7 imaged by the imaging apparatus 1 is defined as the front side of the correction device 7.

As shown in FIGS. 4A, 4B, and 4C, the correction device 7 includes the plate part 31, the color sample part 32, and the support part 33.

Plate Part 31

The plate part 31 is a plate-shaped part. The plate part 31 has a roughly rectangular shape and has a recessed portion on the upper side. The shape of the recessed part is formed, for example, so as to follow the contour of a typical human chin. That is, the upper side of the plate part 31 is formed in a shape such that the face of the subject X is not hidden by the plate part 31. The plate part 31 is formed of a non-deformable material such as a synthetic resin, plastic material, or thick paper.

As shown in FIGS. 4A and 4C, the color sample part 32 is fixed to the front side of the plate part 31 and at the substantially central portion of the plate part 31. The color sample part 32 has a three-dimensional shape, and more specifically, for example, a semi-cylindrical shape. The color sample part 32 is formed of a material that does not deform when it is touched by a hand, and more specifically a material al such as synthetic resin, plastic, metal, or wood.

There is a possibility that the brightness of the room changes due to deterioration of the lighting in the room where the imaging apparatus 1 is installed, a change in the lighting, a change in the layout of the room, or the like, which may cause a change in the colorimetric value acquired by of the imaging apparatus 1. The brightness of light hitting the subject X may change also due to the movement of a person in the room, which may cause a change in the colorimetric value acquired by of the imaging apparatus 1.

To handle the above situation, the imaging apparatus 1 generates reference data from the still image data of the color sample part 32 of the correction device 7 imaged in the preparatory operation, and stores the generated reference data in the storage unit 12. The imaging apparatus 1 compares the still image data of the color sample part 32 of the correction device 7 imaged in the normal operation with the reference data stored in the storage unit 12, and corrects the colorimetric value of the cheek of the subject X based on the result of the comparison.

For example, the control unit 11 captures the still image of the correction device 7 in the preparatory operation. The control unit 11 acquires a predetermined number of pieces of pixel information selected in order of brightness from the brightest from the pixel information (for example, RGB signals) of the captured image of the color sample part 32 of the correction device 7, and stores the acquired pixel information as the reference data in the storage unit 12. More specifically, for example, the control unit 11 acquires top 20% of the highest-brightness pixels from the pixel information of the captured image of the color sample part 32 of the correction device 7, and stores the acquired pixel information as the reference data in the storage unit 12.

The control unit 11 captures a still image of the face of the subject X and the correction device 7 in the normal operation. The control unit 11 acquires pixel information by selecting a predetermined number of pieces of highest-brightness pixel information from the pixel information of the captured image of the color sample part 32 of the correction device 7. More specifically, for example, the control unit 11 acquires top 20% of the highest-brightness pixels from the pixel information of the captured image of the color sample part 32 of the correction device 7.

The control unit 11 compares the acquired pixel information with the reference data stored in the storage unit 12. The control unit 11 corrects the colorimetric value of the cheek of the subject X imaged together with the correction device 7 based on the comparison result.

That is, the control unit 11 compares the image data of the color sample part 32 of the correction device 7 imaged in the normal operation with the reference data stored in the preparatory operation thereby detecting a change in the brightness of the environment in which the imaging apparatus 1 is installed. Then, the control unit 11 corrects the colorimetric value of the cheek of the subject X imaged together with the correction device 7 according to the change in the brightness of the environment in which the imaging apparatus 1 is installed.

Note that the color sample part 32 has a three-dimensional shape, and thus, when light strikes the color sample part 32 from various directions, the intensity of light with the highest brightness among light reflected from the color sample part 32 is constant.

For example, in a case where the color sample part 32 has a semi-cylindrical shape, when the color sample part 32 is illuminated with light emitted from the ceiling, the brightness of the color sample part 32 as seen from the camera 4 is constant even when the hand-holding angle of the correction device 7 fluctuates up or down. If the color sample part 32 is formed to be flat, the brightness of the color sample changes depending on the state in which it is held, and more specifically, the color sample looks dark when it is faced down and the color sample looks bright when it is faced up. Such a problem can be solved by forming the color sample part 32 in the three-dimensional shape.

In the above description, the control unit 11 acquires the predetermined number of pieces of highest-brightness pixel information from the pixel information of the captured image of the color sample part 32 of the correction device 7, but this is merely an example. To remove a shine, the control unit 11 may acquire a predetermined number of pixel information excluding the brightest pixel information from the pixel information of the captured image of the color sample part 32 of the correction device 7. More specifically, for example, the control unit 11 acquires pixel information by selecting pixel information with brightness in a range from a 5% high level to 25% high level from the captured image of the color sample part 32 of the correction device 7.

Support Part 33

As shown in FIGS. 4B and 4C, the support part 33 is fixed to the substantially central portion of the plate part 31 on the back surface side of the plate part 31. The support part 33 has a semi-cylindrical shape.

When the correction device 7 is placed under the chin of the subject X, the support part 33 comes into contact with the lower part of the chin of the subject X (see, for example, FIG. 3B). Therefore, it is desirable that the support part 33 is formed of a soft material such as a sponge.

Placing the support part 33 so as to come into contact with the bottom of the chin of the subject X causes the position of the correction device 7 in the vertical direction to be restricted (determined) under the chin of the subject X.

Protrusion 41 of Plate Part 31

As shown in FIGS. 4A and 4B, the plate part 31 has a protrusion 41 formed so as to extend upward from the lowermost portion of the recessed portion on the upper side of the plate part 31. The correction device 7 is placed such that the protrusion 41 is in contact with the tip of the chin of the subject X (see, for example, FIG. 3A). This causes the position of the correction device 7 to be restricted (determined) in the front direction of the subject X under the chin of the subject X. Restricting the position of the correction device 7 makes it possible to prevent the color sample part 32 from being hidden under the chin.

Patterns 42 and 43 of Plate Part 31

As shown in FIG. 4A, two-dimensional patterns 42 and 43 are drawn on the surface side of the plate part 31. The patterns 42 and 43 are drawn at locations a certain distance apart from each other in the left-right direction.

Depending on the distance between the main body 2 and the correction device 7, the brightness of the illumination light that hits the subject X may change, and thus the colorimetric value measured by the imaging apparatus 1 may change. Depending on the up-down or right/left orientation of the correction device 7 with respect to the main body 2, the brightness of the illumination light that hits the subject X may change, and thus the colorimetric value measured by the imaging apparatus 1 may change.

To handle the above situation, the imaging apparatus 1 generates reference data (different from the reference data generated from the image data of the color sample part 32) from still image data of the patterns 42 and 43 of the correction device 7 imaged in the preparatory operation, and stores the generated reference data in the storage unit 12. The imaging apparatus 1 compares still image data of the patterns 42 and 43 of the correction device 7 imaged in the normal operation with the reference data, and corrects the colorimetric value of the cheek of the subject X based on the result of the comparison.

For example, the control unit 11 captures the still image of the correction device 7 in the preparatory operation. The control unit 11 recognizes the patterns 42, 43 on the plate part 31 of the correction device 7 in the still image using, for example, pattern matching.

The control unit 11 calculates the position of the correction device 7 in the two-dimensional directions by using the recognized positions of the patterns 42 and 43. For example, the control unit 11 calculates the position (the two-dimensional position) of the correction device 7 in the left/right and up/down directions in the still image captured by the camera 4.

Further, the control unit 11 calculates the distance between the correction device 7 and the main body 2 based on the recognized distance between the patterns 42 and 43. Alternatively, the control unit 11 may calculate the distance between the correction device 7 and the main body 2 based on the sizes of the recognized patterns 42 and 43.

The control unit 11 stores the two-dimensional position and the distance of the correction device 7 calculated in the preparatory operation as reference data in the storage unit 12.

The control unit 11 captures a still image of the face of the subject X and the correction device 7 in the normal operation. The control unit 11 recognizes the patterns 42 and 43 on the plate part 31 of the correction device 7 in the still image using, for example, pattern matching.

The control unit 11 calculates the position of the correction device 7 in the two-dimensional directions by using the positions of the recognized patterns 42 and 43. For example, the control unit 11 calculates the two-dimensional position of the correction device 7 in the still image captured by the camera 4.

Furthermore, the control unit 11 calculates the distance between the correction device 7 and the main body 2 based on the distance between the recognized patterns 42 and 43. Alternatively, the control unit 11 may calculate the distance between the correction device 7 and the main body 2 based on the sizes of the recognized patterns 42 and 43.

The control unit 11 compares the calculated two-dimensional position and the distance with the reference data stored in the storage unit 12. The control unit 11 corrects the colorimetric value of the cheek of the subject X imaged together with the correction device 7 based on the comparison result.

It is preferable that the patterns 42 and 43 are different from each other. This makes it possible for the control unit 11 to recognize that the patterns 42 and 43 are different from each other without confusion in the process of recognizing the patterns 42 and 43 by pattern matching or the like. Since the control unit 11 can recognize that the patterns 42 and 43 are different from each other without confusion, the control unit 11 can correctly acquire the coordinate information or the like for each of the patterns 42 and 43 individually.

The patterns 42 and 43 are not limited to the examples shown in FIG. 4A. The patterns 42 and 43 may be lines, illustrations, photographs, characters, symbols, figures, geometric patterns, and combinations of two or more thereof.

In a case where the patterns 42 and 43 are the same, the control unit 11 adjusts the search (scan) start position and the direction of the matching.

Frame Pattern 44 of Plate Part 31

As shown in FIG. 4A, a frame pattern 44 is drawn on the front surface of the plate part 31 and along the outer edge of (surrounding the outer edge of) of the color sample part 32. In the example shown in FIG. 4A, the color sample part 32 has a semi-cylindrical shape, and the frame pattern 44 drawn on the plate part 31 has a quadrilateral shape. The width W1 of the base of the frame pattern 44 is drawn wider than the width W2 of the upper side.

For example, as shown in FIG. 1, the camera 4 is disposed above the main body 2 and so as to be capable of imaging the subject X sitting on a chair from above looking down. Since the width of the base of the frame pattern 44 is drawn wider than the width of the upper side, when the subject X places the correction device 7 under the chin and holds the correction device 7 in an appropriate direction, the image of the quadrilateral frame pattern 44 is captured by the camera 4 such that the widths of the four sides of the square frame pattern 44 are substantially equal.

For example, the subject X places the correction device 7 under the chin and holds the correction device 7 such that the normal line of the plate part 31 extends in a horizontal direction. In this case, when the camera 4 captures the image of the frame pattern 44 with the quadrilateral shape, the four sides of the quadrilateral frame pattern 44 have the substantially the same width in the image (see, for example, FIG. 5A). In a case where the subject X puts the correction device 7 under the chin and holds it such that the normal line of the front surface of the plate part 31 faces downward, the bottom of the quadrilateral frame pattern 44 is hidden by the color sample part 32, and the bottom of the quadrilateral frame pattern 44 is not included in the image captured by the camera 4 (see, for example, FIG. 5D).

Figure 5A:
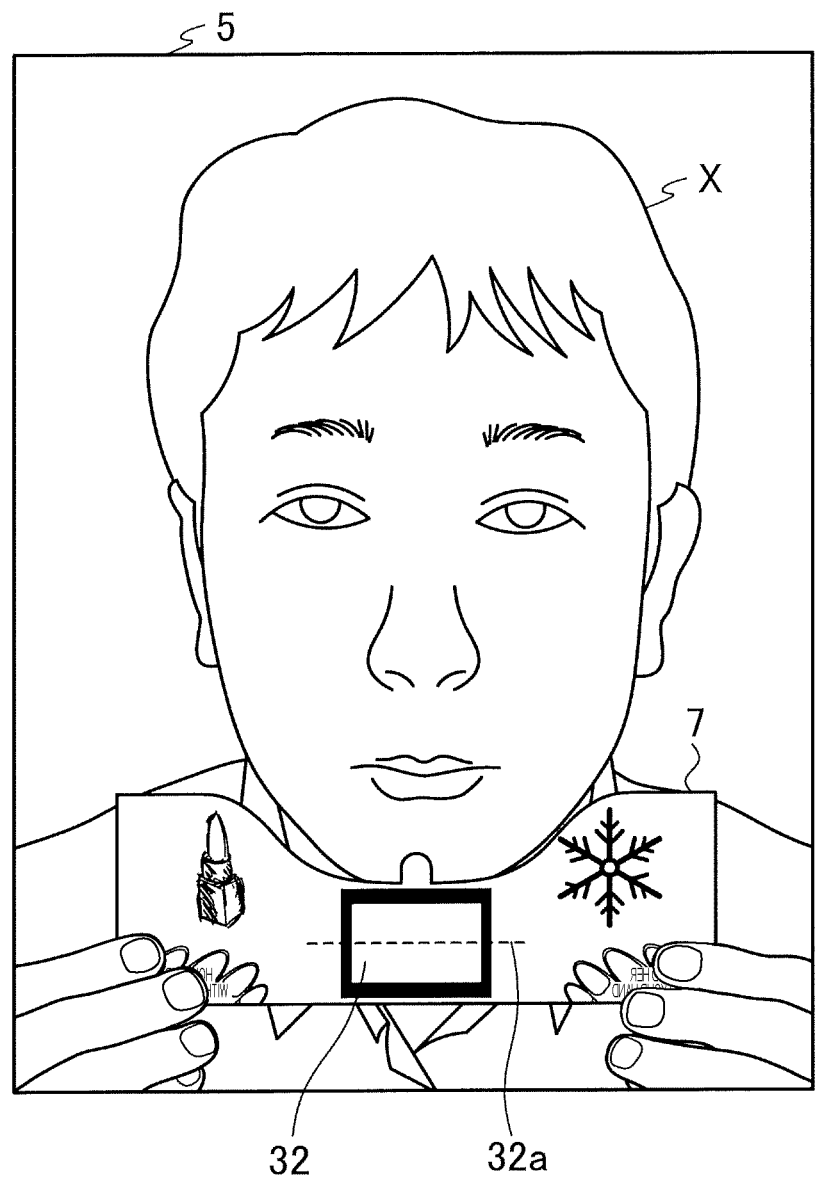
FIG. 5A is a diagram showing an example of an appropriate posture state of a correction device.
Figure 5B:
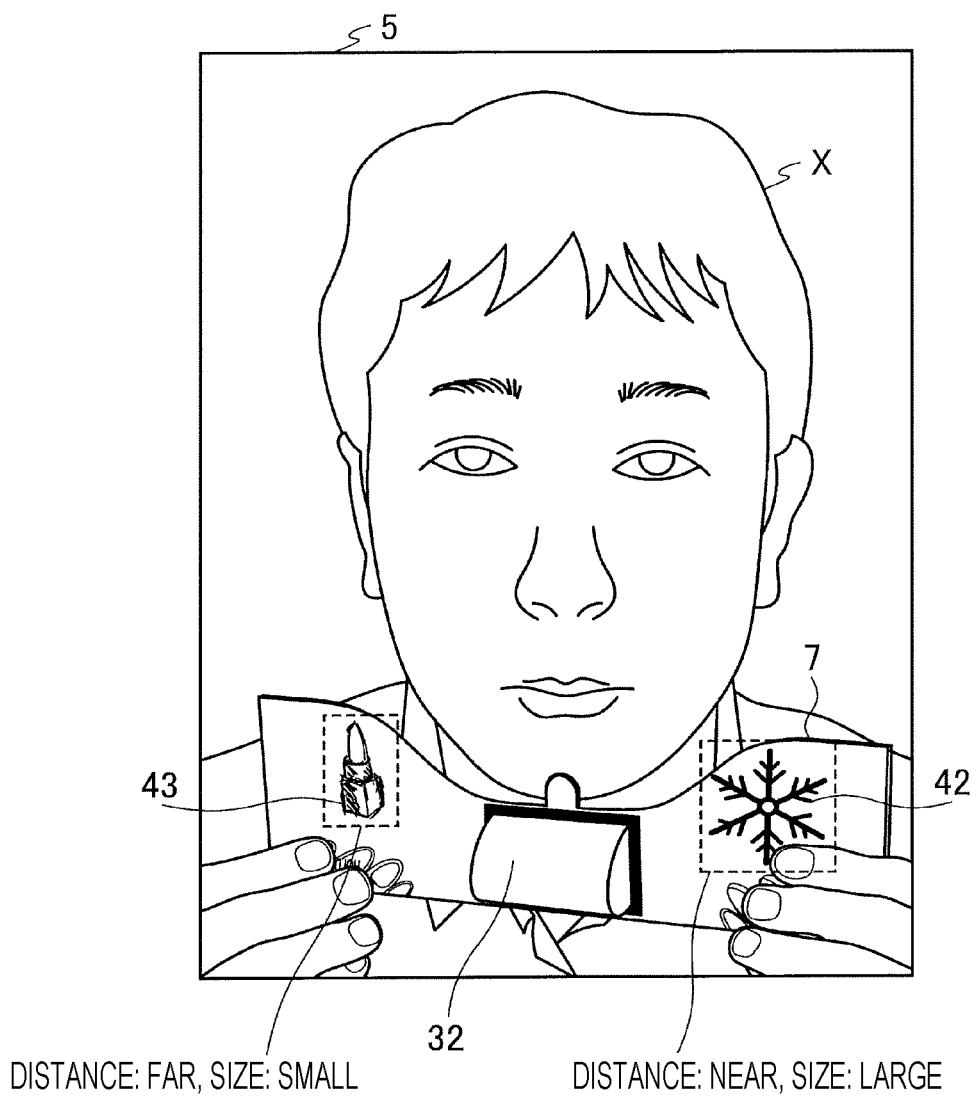
FIG. 5B is a diagram showing an example of an inappropriate posture state of a correction device.

In a case where the subject X puts the correction device 7 under the chin and holds it such that the normal line of the front surface of the plate part 31 deviates from the front direction of the main body 2 into a left or right direction, a left or right side of the frame pattern 44 is hidden by the color sample part 32, and the left or right side of the quadrilateral frame pattern 44 is not captured by the camera 4 (see, for example, FIG. 5B).

Figure 5C:
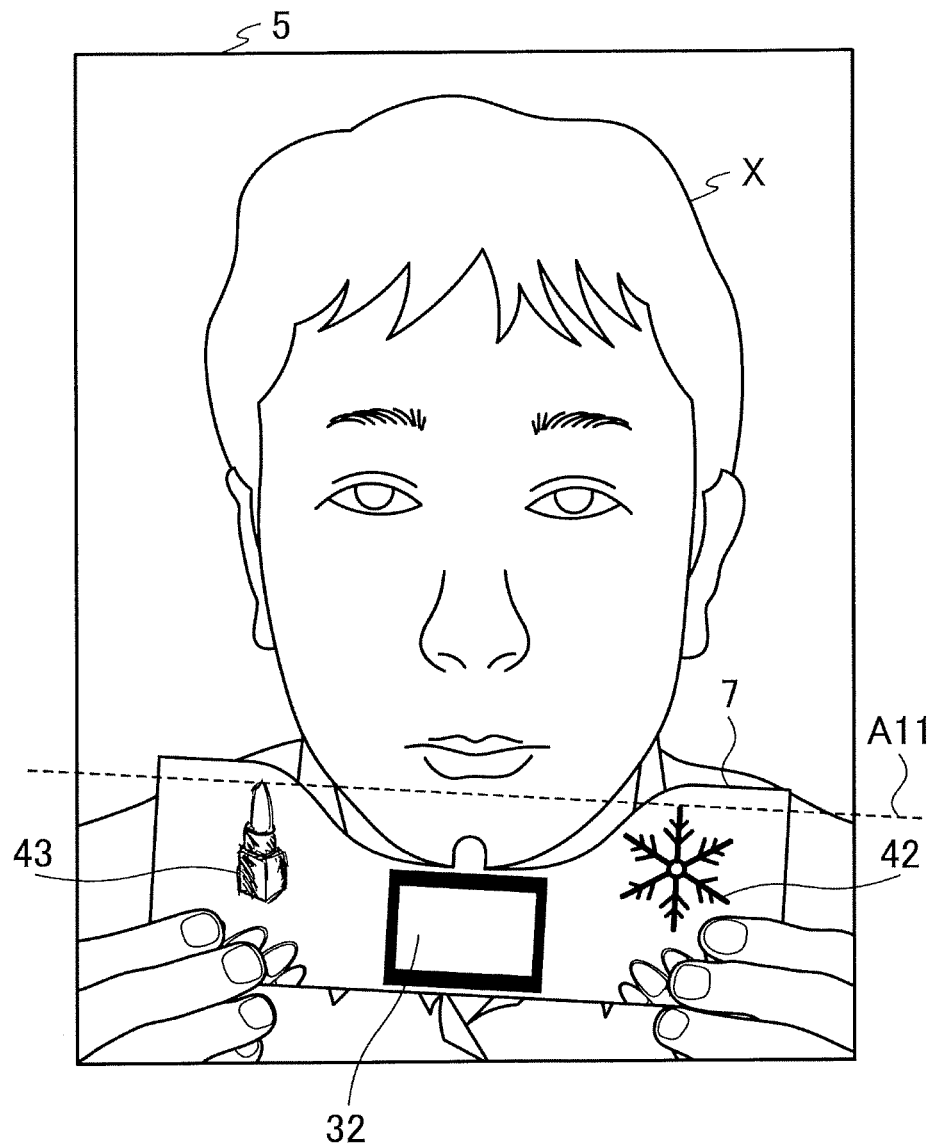
FIG. 5C is a diagram showing an example of an inappropriate posture state of a correction device.

In a case where the subject X puts the correction device 7 under the chin and holds it such that the plate part 31 is tilted (rotated), the top and bottom sides of the frame pattern 44 are no longer horizontal, and the left and right sides are no longer vertical (see, for example, FIG. 5C).

Therefore, the control unit 11 can determine, from the image of the frame pattern 44 captured by the camera 4, whether or not the subject X appropriately holds the correction device 7. That is, the control unit 11 can determine whether the correction device 7 is held in a correct posture from the image of the frame pattern 44.

For example, when the bottom of the frame pattern 44 is not included in the captured image, the control unit 11 may display an instruction on the display 5 to prompt to move the direction of the correction device 7 upward. For example, when the upper side of the frame pattern 44 is not included in the captured image, the control unit 11 may display an instruction on the display 5 to prompt to move the direction of the correction device 7 downward. When the left or right side of the frame pattern 44 is not included in the captured image, the control unit 11 may display an instruction on the display 5 to prompt to move the direction of the correction device 7 to the right or left. When the upper and lower sides of the frame pattern 44 are not horizontal and the left and right sides are not vertical, the control unit 11 may display an instruction on the display 5 to prompt to rotate the correction device 7 in a clockwise or counterclockwise direction.

Designs 45 to 48 on Plate Part 31

As shown in FIG. 4A, designs 45 and 46 representing left and right hands drawn on the front side of the plate part 31. As shown in FIG. 4B, designs 47 and 48 representing left and right hands are drawn on back side of the plate part 31. The subject X is supposed to grip the plate part 31 at portions where the designs 45 to 48 of hands are drawn. Thus, the correction device 7 is grasped by the subject X with both hands, and the position thereof can be easily adjusted.

The designs 45 to 48 each may be formed in a three-dimensional shape for being held by the subject X. For example, the designs 45 to 48 each may be formed in a three-dimensional shape in which fingers of the subject X can be fitted.

The size of the correction device 7 may be determined based on the width of the face or the head of the subject X and the size of the screen of the display 5 (the angle of view of the camera 4). In a case where the subject X is Japanese, the width of the head is in a range from about 13 to about 18 cm, and thus the width of the correction device 7 may be about 20 cm including areas of portions gripped by the subject X.

The average face size varies depending on the race, the gender, the age, etc. Therefore, the size of the correction device 7 may be changed depending on the race, the gender, the age, and/or the like of the subject X who uses the correction device 7.

The area size of the color sample part 32 is set to be large enough so that the influence of noise of the camera 4 can be neglected. For example, the number of pixels of the color sample part 32 in the image captured by the camera 4 is set to a value that is large enough with respect to the total number of pixels of the captured image such that the influence of noise on the color sample part 32 in the image can be negligibly small. Specifically, it is preferable that the number of pixels of the color sample part 32 in the image is equal to or larger than 100. More specifically, it is preferable to form the color sample part 32 such that the length of one side is equal to or larger than 1 cm and equal to or smaller than 5 cm. In a case where the color sample part 32 has a three-dimensional shape, the number of pixels used for image processing is smaller than that of the color sample part with the flat shape. In view of the above, when the color sample part 32 has a three-dimensional shape, the size of the color sample part 32 may be slightly increased.

The color sample part 32 is preferably set to have a height that does not cause a shadow to be cast by a bulge of the nose or cheeks of the subject X. For example, when it is assumed that the height of the nose of a general person is in a range from 2.5 cm to 3 cm, the height of the color sample part 32 is preferably set to 3 cm or greater.

Two or more color sample parts 32 may be provided. In this case, the control unit 11 may execute the process using the average value of the image data of the plurality of color sample parts 32.

It is preferable that the sizes of the patterns 42 and 43 are set to values that allow the pattern matching algorithm to execute, with high performance, the pattern matching for the angle of view with which the face of the subject X is imaged. To avoid the patterns 42 and 43 from being too large to fit in the angle of view of the camera 4, the patterns 42 and 43 are preferably drawn within the range of size from 2 cm to 5 cm.

The distance between the pattern 42 and the pattern 43 is used to calculate the distance between the subject X and the main body 2. To appropriately calculate the distance between the subject X and the main body 2, the distance between the pattern 42 and the pattern 43 is preferably set to be approximately equal to the width of a human face.

When the brightness (luminance) of the colorimetric value is corrected, one of RGB colors may be monitored. Therefore, the color of the color sample part 32 may be selected such that at least one of GRB colors has a gradation level which does not cause overexposure. On the other hand, in a case where a correction is made for each of measured RGB colors, that is, in a case where the correction is made for each color component (hue, saturation, etc.), the color of the color sample part 32 may be selected such that the selected color has a gradation level which does not cause overexposure for any of three RGB colors. For example, a gray color in a range from about 20% level to 80% level may be selected as the color of the color sample part 32.

It is preferable that the surface of the color sample part 32 is matte-processed to prevent an occurrence of specular reflection of lighting or the like.

The shape of the color sample part 32 is not limited to the semi-cylindrical shape. The shape of the color sample part 32 may be a cylindrical shape, aspherical shape, an elliptical spherical shape, a square shape, a partial cylindrical shape, a partial spherical shape, a partial elliptical spherical shape, or a combination of two or more thereof.

In a case where the color sample part 32 of the correction device 7 has a semi-cylindrical shape, a cylindrical shape, or the like, the color sample part 32 reflects illumination light upward or downward uniformly in various directions. In a case where the color sample part 32 has a semi-cylindrical shape or a cylindrical shape, the correction device 7 is capable of handling shaking in the vertical direction. In a case where the color sample part 32 of the correction device 7 has a hemispherical shape, a spherical shape, or the like, the color sample part 32 reflects illumination light upward or downward uniformly in various directions. In a case where the color sample part 32 has a hemispherical shape, a spherical shape, or the like, the correction device 7 is capable of handling up-down shaking caused by hand shaking.

In the above description, the control unit 11 determines whether the correction device 7 is in an appropriate posture based on the image of the frame pattern 44, but the control unit 11 may make the determination by using the images of the patterns 42 and 43.

Figure 5D:
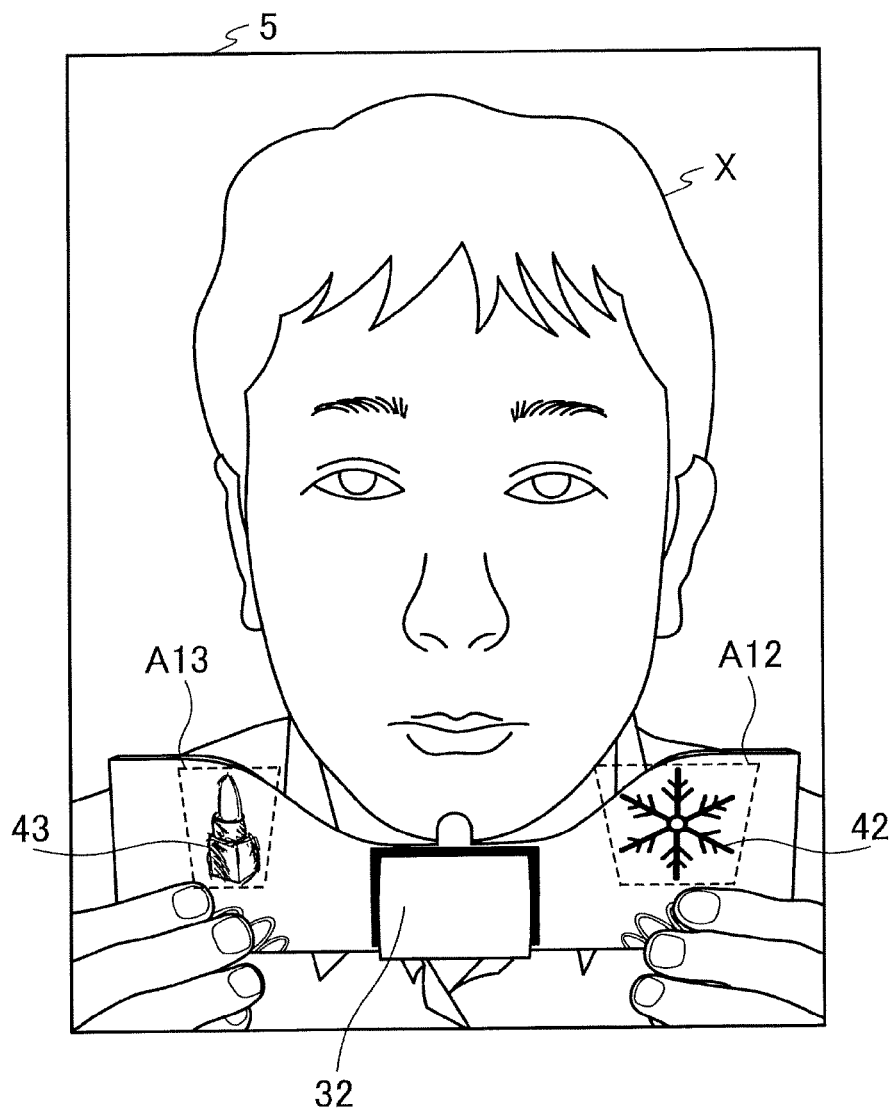
FIG. 5D is a diagram showing an example of an inappropriate posture state of a correction device.

FIG. 5A is a diagram showing an example of an appropriate posture state of the correction device 7. FIGS. 5B, 5C, and 5D each show an example of an improper posture state of the correction device 7.

In a case where the subject X appropriately grasps the correction device 7 as shown in FIG. 5A, an axis 32a (a central axis of a semi-cylinder) indicated by a broken line of the color sample part 32 is horizontal, and parallel to the main body 2 of the imaging apparatus 1, and furthermore, the normal line of the plate part 31 of the correction device 7 is horizontal.

In a case where the subject X grips the correction device 7 such that the direction of the correction device 7 shifts to the left or right, a change in size between the pattern 42 and the pattern 43 occurs. In a case where the subject X holds the correction device 7, for example, such that the pattern 42 is close to the main body 2 and the pattern 43 is far from the main body 2 as shown in FIG. 5B, the size of the pattern 42 is larger than the size of the pattern 43. Therefore, the control unit 11 can determine, from the sizes of the patterns 42 and 43, whether the subject X holds the correction device 7 in a direction shifted to the left or right.

In a case where the subject X grips the correction device 7 such that the correction device 7 tilts (rotates), a difference in height occurs between the pattern 42 and the pattern 43. For example, in a case where the subject X grips the correction device 7 such that the correction device 7 is tilted (rotated), and more specifically such that the position of the pattern 42 is lower than that of the pattern 43 as shown in FIG. 5C, the top of the pattern 42 is lower than the top of the pattern 43 as indicated by a broken line A11 shown in FIG. 5C. Therefore, the control unit 11 can determine, from the heights of the patterns 42 and 43, whether the subject X is holding the correction device 7 in a posture tilted in a clockwise or counterclockwise direction.

In a case where the subject X grips the correction device 7 in a direction facing upward or downward, the shapes of the patterns 42 and 43 are distorted with respect to the shapes obtained when the correction device 7 faces in the front direction. For example, in case where the subject X holds the correction device 7 in a direction facing downward as shown in FIG. 5D, the patterns 42 and 43 are distorted into trapezoidal shapes as indicated by broken-line frames A12 and A13 in FIG. 5D. Therefore, the control unit 11 can determine, from the distortions of the patterns 42 and 43, whether the correction device 7 is held by the subject X in a direction facing upward or downward.

In the normal operation, the ROI identification unit 21 identifies, for example, a cheek of the subject X from a still image captured by the camera 4. In a case where a blemish is detected, a blemish part may be excluded from the identified cheek.

Figure 6A:
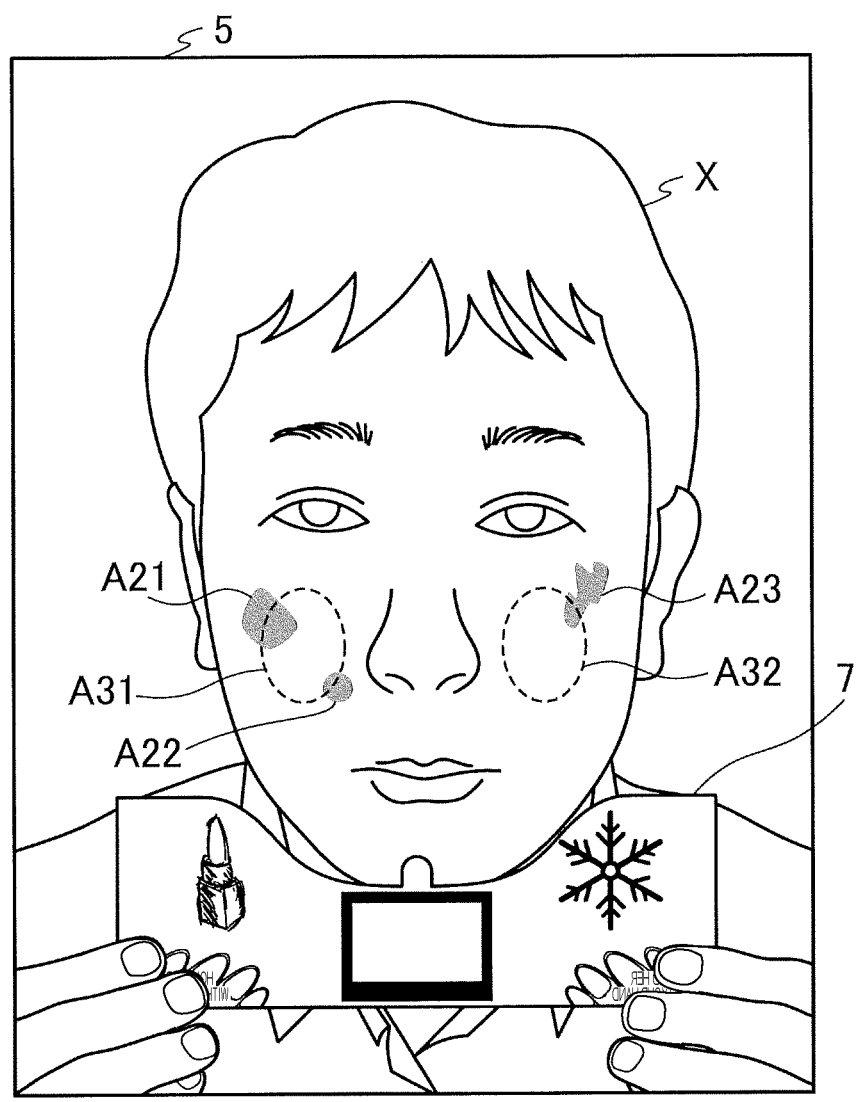
FIG. 6A is a diagram illustrating an example of an operation of an ROI identification unit.
Figure 6B:
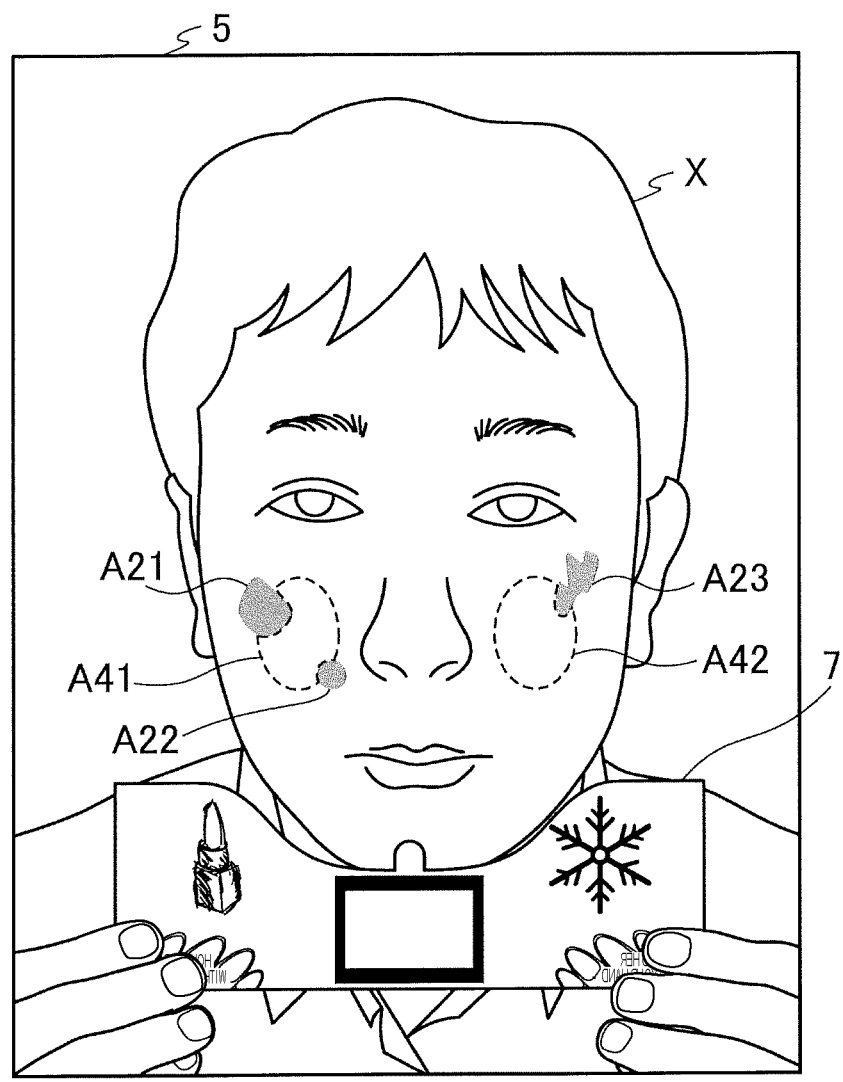
FIG. 6B is a diagram illustrating an example of an operation of an ROI identification unit.

An example of an operation of the ROI identification unit 21 is described below with reference to FIGS. 6A and 6B. In FIGS. 6A and 6B, A21 to A23 each denote a blemish.

The ROI identification unit 21 identifies cheeks of a face of the subject X by an image recognition process. For example, the ROI identification unit 21 identifies the cheeks of the face of the subject X as indicated by broken-line frames A31 and A32 in FIG. 6A.

When the ROI identification unit 21 identifies the cheeks of the subject X, the ROI identification unit 21 detects blemishes A21 to A23 in the identified cheek parts (areas) of the subject X by the image recognition process. The RIO identification unit 21 further identifies areas, in the identified cheek parts, obtained by excluding the detected blemishes A21 to A23 from the cheek parts. For example, the ROI identification unit 21 identifies the cheeks of the face of the subject X so as not to include the blemish parts A21 to A23, as indicated by broken-line frames A41 and A42 in FIG. 6A.

In other words, the ROI identification unit 21 identifies the cheek areas such that there is no overlap with the blemish parts A21 to A23.

The control unit 11 performs the color measurement for the cheek areas excluding the blemish parts A21 to A23 and makes a correction using a correction value. This makes it possible, for example, for the control unit 11 to propose a cosmetic or the like suitable for the subject X based on the colorimetric value of the cheeks excluding the blemish parts A21 to A23.

In the above description, the ROI identification unit 21 excludes the blemish parts from the identified cheeks, but this is merely by way of example but not limitation. For example, the ROI identification unit 21 may exclude, from the identified cheeks, at least one of the following: a blemish; a wrinkle; a scar, and a disorder.

The ROI identification unit 21 may define, as a cheek part, an area where an originally identified cheek area overlaps with one or more detected blemish areas A21 to A23. The control unit 11 may determine a skin condition of a part (a blemish part) in the identified cheek area by an image recognition process.

Figure 7:
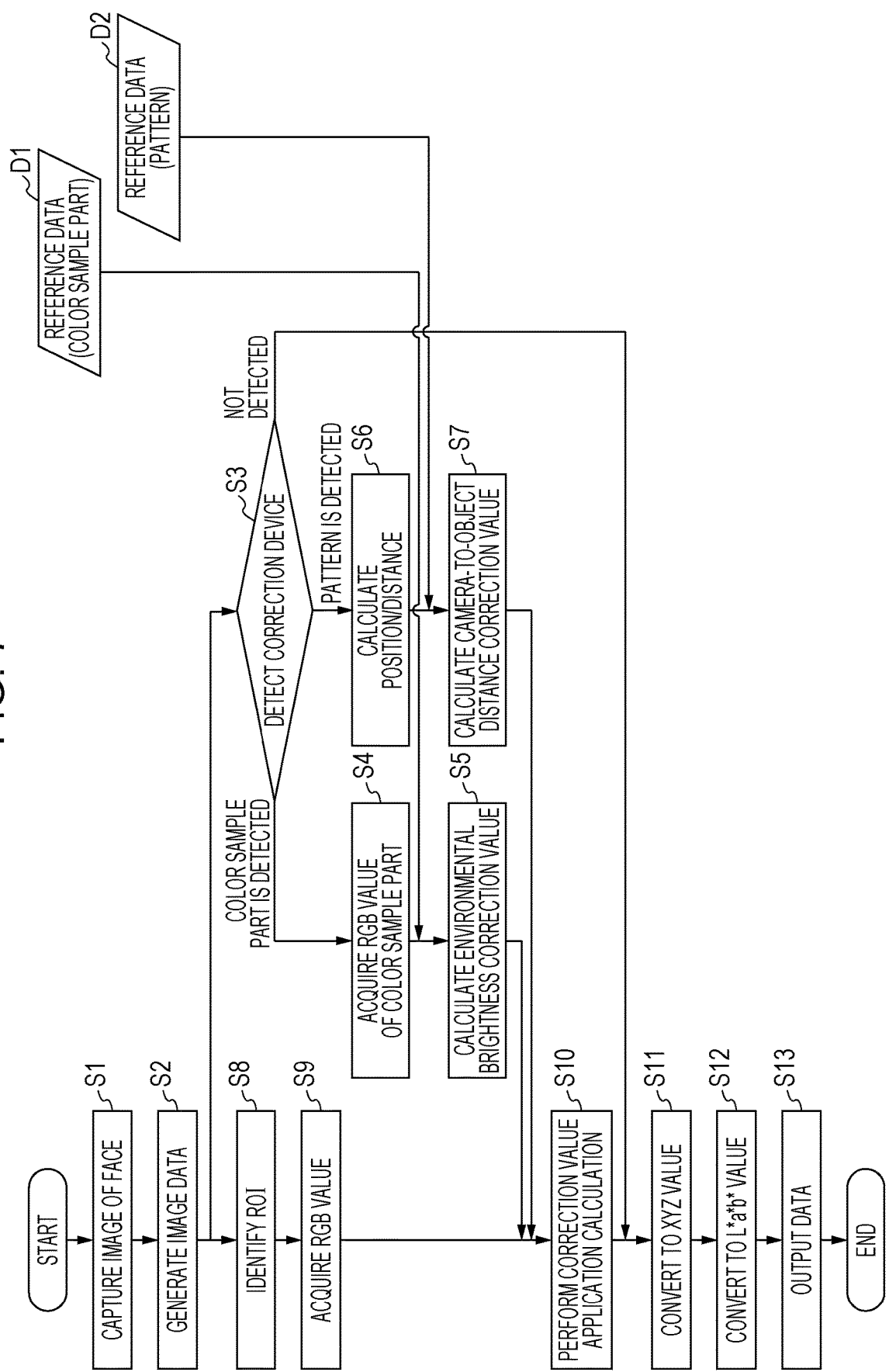
FIG. 7 is a flowchart illustrating an example of an operation of an imaging apparatus.

FIG. 7 is a flowchart showing an example of an operation of the imaging apparatus 1. It is assumed that the imaging apparatus 1 acquires reference data D1 associated with the color sample part 32 and stores it in the storage unit 12 in the preparatory operation. It is also assumed that the imaging apparatus 1 acquires reference data D2 associated with by the patterns 42 and 43 and stores it in the storage unit 12 in the preparatory operation. When the input apparatus 6 accepts an imaging operation by the subject X, the process is performed as follows.

The control unit 11 captures an image of a face of the subject X using the camera 4 (S1). For example, when the subject X appropriately holds the correction device 7 under the chin of the subject X, and when the face of the subject X comes within the angle of view of the camera 4, the control unit 11 captures an image of the face of the subject X using the camera 4.

The control unit 11 generates image data as a result of capturing the image in S1 (S2). The image data is generated in the form of still image data.

The control unit 11 determines whether or not the correction device 7 is detected from the image data generated in S2 (S3). In a case where the correction device 7 is detected from the image data generated in S2, if the color sample part 32 of the correction device 7 is detected (if it is determined in S3 that the color sample part is detected), the control unit 11 advances the process to S4. When the correction device 7 is detected from the image data generated in S2, if patterns 42 and 43 of the correction device 7 are detected (if it is determined in S3 that patterns are detected), the control unit 11 advances the process to S6. Note that when the correction device 7 is detected from the image data generated in S2, if the color sample part 32 and the patterns 42 and 43 of the correction device 7 are detected (if it is determined in S3 that the color sample part is detected and the patterns are detected), the control unit 11 executes processes in S4 and S5 and processes in S6 and S7. In a case where the correction device 7 is not detected (in a case where it is determined in S3 that the correction device is not detected), the control unit 11 advances the process to S11.

In the case where it is determined in S3 that the color sample part 32 is detected, the control unit 11 acquires an RGB value of the color sample part 32 from the image data generated in S2 (S4).

The control unit 11 compares the RGB value of the color sample part 32 acquired in S4 with the reference data D1 stored in the storage unit 12, and calculates a correction value for correcting the colorimetric value (S5).

In the case where it is determined in S3 that the patterns 42 and 43 are detected, the control unit 11 calculates, from the image data generated in S2, the two-dimensional position of the correction device 7 and the distance of the correction device 7 from the main body 2 (S6).

The control unit 11 compares the two-dimensional position of the correction device 7 calculated in S6 and the main body 2 with the reference data D2 stored in the storage unit 12, and calculates a correction value for correcting the colorimetric value (S7).

The control unit 11 identifies a cheek of the subject X from the image data generated in S2 (S8).

The control unit 11 acquires an RGB value from the image data of the cheek identified in S8 (S9).

The control unit 11 corrects the RGB value acquired in S9 by using the correction value calculated in S5 (S10). Furthermore, the control unit 11 corrects the RGB value acquired in S9 by using the correction value calculated in S7 (S10).

The control unit 11 converts the RGB value acquired in S10 into an XYZ value (S11). In the case where it is determined in S3 that neither the color sample part 32 of the correction device 7 nor the patterns 42 and 43 of the correction device 7 are detected (in the case where it is determined in S3 that the correction device is not detected), the control unit 11 converts the RGB value acquired in S9 into the XYZ value.

The control unit 11 converts the RGB value acquired in S10 into an L*a*b* value (S12). In the case where it is determined in S3 that neither the color sample part 32 of the correction device 7 nor the patterns 42 and 43 of the correction device 7 are detected (in the case where it is determined in S3 that the correction device is not detected), the control unit 11 converts the RGB value acquired in S9 into an L*a*b* value.

The control unit 11 outputs data, for example, to the external device 13 (S13). For example, the control unit 11 outputs the XYZ value converted in S11 to the external device 13. The control unit 11 also outputs the L*a*b* value converted in S12 to the external device 13.

Note that when it is determined in S3 that the correction device 7 is detected, if neither the color sample part 32 of the correction device 7 nor the patterns 42 and 43 of the correction device 7 are detected (in the case where it is determined in S3 that nothing is detected), the control unit 11 may advance the process to S11.

The control unit 11 may execute the processes in S8 and S9 in parallel with the processes from S3 to S7. The control unit 11 may execute the processes from S3 to S7 after the processes in S8 and S9. The control unit 11 may execute the processes in S8 and S9 after the processes from S3 to S7.

When the correction device 7 is detected in S3, if the color sample part 32 and the patterns 42 and 43 of the correction device 7 are detected, the control unit 11 may execute the process in S4 and S5 in parallel with the processes in S6 and S7. The control unit 11 may execute the processes in S6 and S7 after executing the processes in S4 and S5. The control unit 11 may execute the processes in S4 and S5 after executing the processes in S6 and S7.

As described above, the imaging apparatus 1 captures an image of a face of a subject X together with the correction device 7 placed under the chin of the subject X, and identifies a part of a cheek, for which the color measurement is to be performed, in the captured image of the face. The imaging apparatus 1 then acquires a colorimetric value of the identified cheek part and corrects the colorimetric value of the cheek using the image of the correction device 7.

Thus, the imaging apparatus 1 is capable of easily and appropriately measuring the color of the cheek of the subject X by taking an image by the camera 4.

The imaging apparatus 1 corrects the colorimetric value that may change caused by a change in lighting or the like. This expands the degree of freedom of a location where the imaging apparatus 1 is installed. For example, the imaging apparatus 1 may be installed in a general living room, a factory, a cosmetic department, a hospital such as a dermatology hospital, an event venue, or the like, and the imaging apparatus 1 is capable of appropriately performing a color measurement without being installed in a completely shielded closed space.

The imaging apparatus 1 is capable of performing the color measurement with high accuracy without using an expensive measuring instrument. The imaging apparatus 1 is capable of performing the color measurement for a wide area at a time, which allows a reduction in the measurement time.

The imaging apparatus 1 is capable of reducing measurement variations which may occur depending on the skills of the operator.

The imaging apparatus 1 may integrally manage information on a skin condition and a skin color in cooperation with, for example, a skin analyzer. This makes it possible for the imaging apparatus 1, for example, to provide a cosmetic product recommendation and diagnostic assistance in cosmetic dermatology.

In the above description, the imaging apparatus 1 corrects the colorimetric value of the human face using the correction device 7, but this is merely an example. For example, the imaging apparatus 1 may correct the colorimetric value of a part other than the face such as a hand, a foot, and an abdomen, by using the correction device 7.

In the above description, the correction device 7 has the color sample part 32 and the patterns 42 and 43, but this is merely by way of example and not limitation. The correction device 7 may have only either the color sample part 32 or the patterns 42 and 43.

The imaging apparatus 1 may correct a colorimetric value of an object by using the correction device.
For example, the imaging apparatus 1 may correct the colorimetric value of a container, a body of a vehicle, or the like by using the correction device.

Figure 8A:
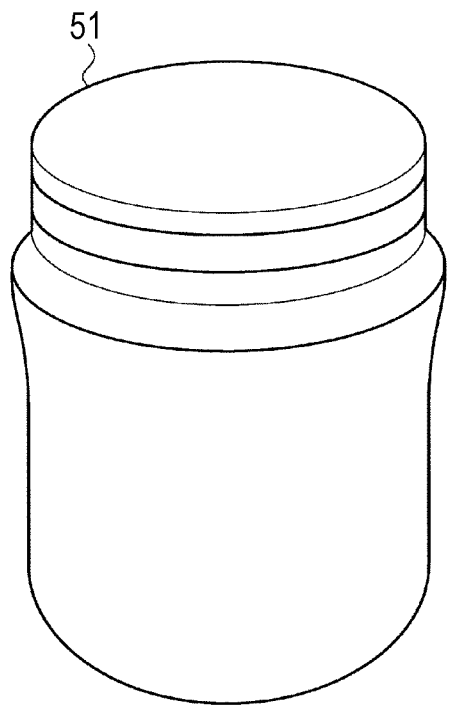
FIG. 8A is a diagram illustrating an example of a container which is to be subjected to a correction of a colorimetric value.
Figure 8B:
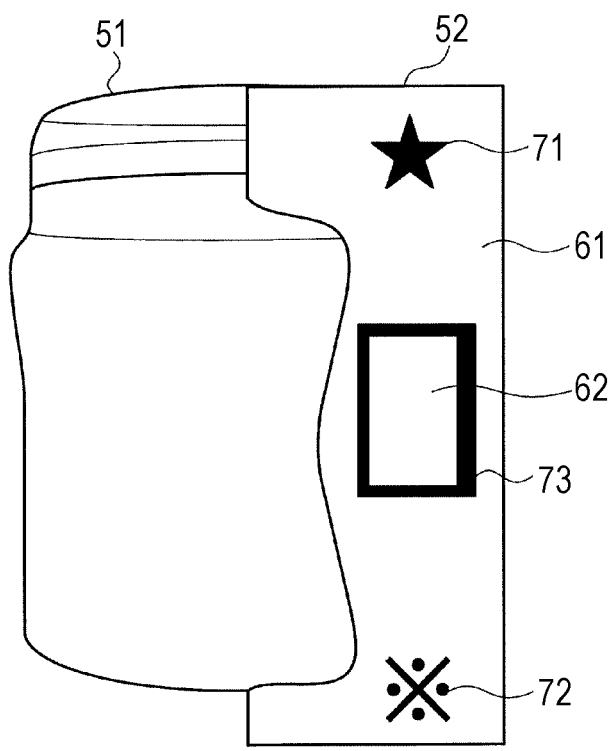
FIG. 8B is a diagram illustrating an example of a manner of correcting a colorimetric value of a container.

Referring to FIGS. 8A and 8B, an example of a manner of correcting a colorimetric value of a container. In FIGS. 8A and 8B, 51 denotes a container subjected to the colorimetric measurement. In FIG. 8B, 52 denotes a correction device that corrects the colorimetric value of the container 51. The correction device 52 has a plate part 61 and a color sample part 62, as with the correction device 7.

The plate part 61 has a recess that fits along the contour (the outer peripheral surface) of the container 51. The correction device 52 is placed such that the recess of the plate part 61 fits with the contour of the container 51. The plate part 61 has patterns 71 and 72 and a frame pattern 73, as with the plate part 31 of the correction device 7.

In a preparatory operation, the imaging apparatus 1 captures an image of the color sample part 62 and stores reference data. Furthermore, in the preparatory operation, the imaging apparatus 1 captures an image of the patterns 71 and 72 and stores reference data thereof.

In a normal operation, the imaging apparatus 1 captures an image of the container 51 and the correction device 52. The imaging apparatus 1 corrects the colorimetric value of the container 51 using the reference data stored in the preparatory operation. As described above, the imaging apparatus 1 is capable of correcting a colorimetric value also for an object other than a person.

In the embodiments described above, notations of " . . . unit" used to denote various constituent elements may be replaced with other notations such as " . . . circuit", " . . . device", " . . . part", " . . . module", or the like.

The present disclosure has been described above with reference to various embodiments in conjunction with the drawing. However, the present disclosure is not limited to these embodiments. As will be apparent to those skilled in the art, various changes and modifications are possible without departing from the scope of the present disclosure as defined by the appended claims. It should be understood that such changes or modifications are also within the technical scope of the present disclosure. Also note that constituent elements of embodiments may be arbitrarily combined as long as a result is within the scope of the present disclosure.

The present disclosure can be realized by software, hardware, or software in cooperation with hardware. Each functional block used in the description of each embodiment described above can be partly or entirely realized by an LSI such as an integrated circuit, and each process described in the each embodiment may be controlled partly or entirely by an LSI or a combination of LSIs. The LSI may be individually formed as chips, or one chip may be formed so as to include a part or all of the functional blocks. The LSI may include an input for inputting data input and an output for outputting data. The LSI may be referred to as an IC, a system LSI, a super LSI, or an ultra LSI depending on a difference in the degree of integration.

However, the technique of implementing an integrated circuit is not limited to the LSI and may be realized by using a dedicated circuit, a general-purpose processor, or a special-purpose processor. In addition, an FPGA (Field Programmable Gate Array) that can be programmed after the manufacture of the LSI or a reconfigurable processor in which the connections and the settings of circuit cells disposed inside the LSI can be reconfigured may be used. The present disclosure can be realized as digital processing or analogue processing.

If future integrated circuit technology replaces LSIs as a result of the advancement of semiconductor technology or other derivative technology, the functional blocks could be integrated using the future integrated circuit technology. Biotechnology may be one of such promising future technologies.

In an aspect, the present disclosure provides an imaging method including capturing an image of a face of a person together with a correction device placed close to the face, identifying a part, for which a color measurement is to be performed, in the image of the face, acquiring a colorimetric value of the part, and correcting the colorimetric value using an image of the correction device.

In the imaging method according to the present disclosure, the colorimetric value of the part may be corrected by using an image of a three-dimensional shape provided in the correction device.

In the imaging method according to the present disclosure, the three-dimensional shape may be a cylindrical shape, a spherical shape, an ellipsoidal spherical shape, a square shape, a partial cylindrical shape, a partial spherical shape, or a partial ellipsoidal spherical shape, or a combination of two or more thereof.

In the imaging method according to the present disclosure, the colorimetric value of the part may be corrected by using an image of a two-dimensional pattern drawn on the correction device.

In the imaging method according to the present disclosure, the two-dimensional pattern may be a pattern of a line, an illustration, a photograph, a character, a symbol, a figure, or a geometric pattern, or a pattern of a combination of two or more thereof.

In the imaging method according to the present disclosure, the part of the face for which the color measurement is performed may be a cheek.

In the imaging method according to the present disclosure, the correction device may be placed close to the face such that the distance between the part for which the color measurement is performed and the imaging apparatus for imaging the face is substantially equal to the distance between the correction device and the imaging apparatus.

In the imaging method according to the present disclosure, the correction device may have a shape fitting along a contour shape of the face.

In the imaging method according to the present disclosure, the capturing of the image of the face together with the correction device may be performed in a state in which the correction device is in contact with a tip of the chin of the face.

In the imaging method according to the present disclosure, in a case where at least one of a wrinkle, a blemish, a wound, and a disorder is detected in the part, a detected portion in the part may be excluded from the part, and the colorimetric value may be corrected for a part remaining without being excluded.

In the imaging method according to the present disclosure, the correction device may have a figure representing a position at which the correction device is to be gripped by the person or a three-dimensional shape for being gripped by the person.

In the imaging method according to the present disclosure, the correction device may have the three-dimensional shape on a plate-shaped part, and a pattern may be drawn on the plate-shaped part along the three-dimensional shape.

In the imaging method according to the present disclosure, a posture state of the correction device may be determined based on the image of the two-dimensional pattern, and the posture state may be notified to the person.

In the imaging method according to the present disclosure, the posture state of the correction device may be determined based on an image of the pattern along the three-dimensional shape drawn on the plate-shaped part, and the posture state may be notified to the person.

In the imaging method according to the present disclosure, when the image of the face is captured together with the correction device placed close to the face, a display of the imaging apparatus may be turned off or a specific screen may be displayed on the display.

In the imaging method according to the present disclosure, in a case where the correction device is not included in the captured image, a colorimetric value of the part may be corrected based on a predetermined condition.

In an aspect, the present disclosure provides an imaging apparatus including a camera that captures an image of a face of a person together with a correction device placed close to the face, and a control unit that identifies a part, for which a color measurement is to be performed, in the image of the face, acquires a colorimetric value of the part, and corrects the colorimetric value by using an image of the control unit.

The present disclosure is useful for an imaging apparatus that performs a colorimetric measurement on a human face.

What is claimed is:

1. An imaging method, comprising:
   capturing an image of a face of a person together with a correction device placed close to the face;
   identifying a part, for which a color measurement is to be performed, in the image of the face;
   acquiring a colorimetric value of the part; and
   correcting the colorimetric value using an image of a three-dimensional shape provided in the correction device,
   wherein the correcting is performed by referring to a predetermined range from an upper brightness level included in pixel information of the image of the three-dimensional shape.

2. The imaging method according to claim 1, wherein the three-dimensional shape is a cylindrical shape, a spherical shape, an ellipsoidal spherical shape, a square shape, a partial cylindrical shape, a partial spherical shape, a partial ellipsoidal spherical shape, or a combination of two or more thereof.

3. The imaging method according to claim 1, wherein the colorimetric value of the part is corrected by using an image of a two-dimensional pattern drawn on the correction device.

4. The imaging method according to claim 3, wherein the two-dimensional pattern is a line, an illustration, a photograph, a character, a symbol, a figure, a geometric pattern, or a combination of two or more thereof.

5. The imaging method according to claim 3, wherein a posture state of the correction device is determined based on the image of the two-dimensional pattern, and the posture state is notified to the person.

6. The imaging method according to claim 1, wherein the part in the image of the face for which the color measurement is performed is a cheek.

7. The imaging method according to claim 1, wherein the correction device is placed close to the face such that a first distance between the part for which the color measurement is performed and an imaging apparatus for capturing the image of the face is substantially equal to a second distance between the correction device and the imaging apparatus.

8. The imaging method according to claim 1, wherein the correction device has a shape fitting along a contour shape of the face.

9. The imaging method according to claim 1, wherein the capturing of the image of the face together with the correction device is performed in a state in which the correction device is in contact with a tip of a chin of the face.

10. The imaging method according to claim 1, wherein, in a case where at least one of a wrinkle, a blemish, a wound, or a disorder is detected in a second part in the image of the face, a detected portion in the second part is excluded from the part, and the colorimetric value is corrected for the part remaining without being excluded.

11. The imaging method according to claim 1, wherein the correction device has a figure representing a position at which the correction device is to be gripped by the person or a three-dimensional shape for being gripped by the person.

12. The imaging method according to claim 1, wherein the correction device has the three-dimensional shape on a plate-shaped part, and a pattern is drawn on the plate-shaped part along the three-dimensional shape.

13. The imaging method according to claim 12, wherein a posture state of the correction device is determined based on an image of the pattern along the three-dimensional shape drawn on the plate-shaped part, and the posture state is notified to the person.

14. The imaging method according to claim 1, wherein, when the image of the face is captured together with the correction device placed close to the face, a display of an imaging apparatus is turned off or a specific screen is displayed on the display.

15. The imaging method according to claim 1, wherein, in a case where the correction device is not included in the captured image, the colorimetric value of the part is corrected based on a predetermined condition.

16. An imaging method, comprising:
    capturing an image of a face of a person together with a correction device placed close to the face;
    identifying a part, for which a color measurement is to be performed, in the image of the face;
    acquiring a colorimetric value of the part; and
    correcting the colorimetric value using an image of the correction device,
    wherein the colorimetric value of the part is corrected by using an image of a two-dimensional pattern drawn on the correction device, and
    a posture state of the correction device is determined based on the image of the two-dimensional pattern, and the posture state is notified to the person.

17. An imaging apparatus comprising:
    a camera that captures an image of a face of a person together with a correction device placed close to the face; and
    a controller that identifies a part, for which a color measurement is to be performed, in the image of the face, acquires a colorimetric value of the part, and corrects the colorimetric value by using an image of a three-dimensional shape provided in the correction device,
    wherein controller corrects the colorimetric value by referring to a predetermined range from an upper brightness level included in pixel information of the image of the three-dimensional shape.

\* \* \* \* \*